US008491915B2

(12) United States Patent
Goodyear et al.

(10) Patent No.: US 8,491,915 B2
(45) Date of Patent: Jul. 23, 2013

(54) HEAT TREATED BACTERINS, AND EMULSION VACCINES PREPARED FROM SUCH HEAT TREATED BACTERINS

(75) Inventors: Mark D. Goodyear, Portage, MI (US); Michael J. Huether, Kalamazoo, MI (US); Ramasamy M. Mannan, Kalamazoo, MI (US); Nancee L. Oien, Kalamazoo, MI (US)

(73) Assignee: AH USA 42 LLC, New York, NY (US)

( * ) Notice: Subject to any disclaimer, the term of this patent is extended or adjusted under 35 U.S.C. 154(b) by 610 days.

(21) Appl. No.: 11/851,951

(22) Filed: Sep. 7, 2007

(65) Prior Publication Data
US 2008/0112970 A1 May 15, 2008

Related U.S. Application Data

(60) Provisional application No. 60/843,665, filed on Sep. 11, 2006.

(51) Int. Cl.

| | |
|---|---|
| *A61K 39/295* | (2006.01) |
| *A61K 38/43* | (2006.01) |
| *A61K 38/46* | (2006.01) |

(52) U.S. Cl.
USPC ...................... 424/201.1; 424/94.1; 424/94.6

(58) Field of Classification Search
None
See application file for complete search history.

(56) References Cited

U.S. PATENT DOCUMENTS

| | | | | |
|---|---|---|---|---|
| 5,084,269 | A | 1/1992 | Kullenberg | |
| 6,248,329 | B1 * | 6/2001 | Chandrashekar et al. | 424/191.1 |
| 2004/0258701 | A1 * | 12/2004 | Dominowski et al. | 424/184.1 |

FOREIGN PATENT DOCUMENTS

| | | |
|---|---|---|
| DE | 37 21 169 | 1/1988 |
| WO | 01/54717 | 8/2001 |
| WO | 03/004052 | 1/2003 |
| WO | 2004/026024 | 4/2004 |
| WO | 2004/026336 | 4/2004 |

OTHER PUBLICATIONS

Ellis Chapter 29 of Vaccines, Plotkin, et al. (eds) WB Saunders, Philadelphia, 1998, especially p. 571.*
Pope et al 1987 Journal of Clinical Microbiology pp. 255-258.*
Patel et al 1964 Journal of Bacteriology vol. 88 No. 4 pp. 877-884.*
Singh et al., "Gln277 and Phe554 residues are involved in thermal inactivation of protective antigen of *Bacillus anthracis*", Biochemical and Biophysical Research Communications, 296(5)1058-1062, 2002.
PCT International Search Report, PCT/IB2007/002553.
Zeigler et al., "Immunization Against Leptospirosis: Vaccine Trials with Heat-Killed Whole Cell and Outer Envelope Antigens in Hamsters", Bulletin of the Pan American Health Organization 1976, 10(2):126-130, 1976.
Tyler et al., "Humoral Response in Neonatal Calves Following Immunization with *Escherichia coli* (Strain J5): the Effects of Adjuvant, Age and Colostral Passive Interference", Veterinary Immunology and Immunopathology, 23:333-344, 1989.
Burns et al., "Evaluation of the Effect of Heating an Oil-Emulsion *Pasteurella multocida* Bacterin on Tissue Reaction and Immunity", Avian Diseases, 47:54-58, 2003.
Choi et al., "Isolation of Lipase-Active Fractions from Ultra-High Temperature-Processed Milk and Their Patterns of Releasing Fatty Acids from Milk Fat Emulsion", J. Dairy Sci., 77(8):2168-2176, 1994.

* cited by examiner

*Primary Examiner* — Vanessa L Ford
*Assistant Examiner* — Nina Archie
(74) *Attorney, Agent, or Firm* — Vyacheslav V. Vasilyev

(57) ABSTRACT

Heat treated bacterins, a method of producing heat treated bacterins, and emulsion vaccines prepared from such heat treated bacterins are disclosed.

15 Claims, 2 Drawing Sheets

FIGURE 1

(A) Particle size analysis of freshly prepared vaccine
containing heat treated Leptospira bacterins at day 0

(B) Particle size analysis of freshly prepared vaccine
containing heat treated Leptospira bacterins at day 60

FIGURE 1

(C) Particle size analysis of freshly prepared vaccine
containing non-heat treated Leptospira bacterins at day 0

(D) Particle size analysis of freshly prepared vaccine
containing non-heat treated Leptospira bacterins at day 60

HEAT TREATED BACTERINS, AND EMULSION VACCINES PREPARED FROM SUCH HEAT TREATED BACTERINS

CROSS-REFERENCE TO RELATED APPLICATIONS

The present application claims the priority of U.S. Provisional Application No. 60/843,665, filed on Sep. 11, 2006. The contents of these priority documents are herein incorporated by reference.

FIELD OF INVENTION

This invention relates generally to the field of vaccines and to methods of stabilizing emulsion vaccines. In particular, this invention relates to heat treated bacterins, a method of producing heat treated bacterins, and emulsion vaccines prepared from such heat treated bacterins.

BACKGROUND OF THE INVENTION

Vaccination is increasingly used to control the infectious diseases in animals. Adjuvants are frequently used in vaccines because they are able to increase the humoral and/or cellular immune response to an antigen. Vaccines are often formulated as emulsions because the emulsion can act as an adjuvant, and has the property of retaining the antigen as a depot at the site of injection. Emulsifiers are commonly used in emulsion vaccines. Besides using emulsifiers, the stability of the emulsion vaccines may also be achieved through reducing the droplet size of the emulsion by mechanical means.

U.S. Pat. No. 5,084,269 relates to an adjuvant formulation containing lecithin in combination with mineral oil, which produces less irritation within the host animal, and simultaneously induces increased systemic immunity. Compositions according to U.S. Pat. No. 5,084,269 are in commercial use under the trade name AMPHIGEN®, a trademark of Pfizer, Inc.

Generally, bacterial antigens are unstable when heated and even brief exposure to elevated temperatures can reduce the activity of the antigens. For example current anthrax vaccines can lose all biological activity with 48 hours at 37° C. (S. Sing, N. Ahuja, V. Chauhan, E. Rajasekaran, W. S. Mohsin, R. Bhat, and R. Bhatnagar; Bioche. Biophys. Res. Commun. 2002 Sep. 6; 295(5):1058-62).

SUMMARY OF INVENTION

This invention relates to heat treated bacterins, a method of producing heat treated bacterins, and emulsion vaccines prepared from such heat treated bacterins. The method comprises heating the bacterin to a temperature of about 35 to about 80° C. to form a heat treated bacterin.

BRIEF DESCRIPTION OF DRAWINGS

FIG. 1 is a particle size analysis chart of freshly prepared vaccine containing heat treated *Leptospira* bacterins on days 0 (A) and day 60 (B) and of non-heat treated *Leptospira* bacterins on day 0 (C) and day 60 (D).

DETAILED DESCRIPTION

Definitions

Acceptable antigenic activity—The term "acceptable antigenic activity" means the ability to induce a protective immune response in vaccinated animals after being challenged or by passing a codified potency test with homologous live organism.

Bacterin—The term "bacterin" means a suspension of killed bacteria which may be used as a component of a vaccine.

Emulsifier—The term "emulsifier" means a substance used to make an emulsion more stable.

Emulsion—The term "emulsion" means a composition of two immiscible liquids in which small droplets of one liquid are suspended in a continuous phase of the other liquid.

Heat treated bacterin—The term "heat treated bacterin" means a bacterin that has been heat treated and which has a lipase activity of 50% or less than the lipase activity before the heat treatment, and has acceptable antigenic activity.

Invert Emulsion—The term "invert emulsion" means a water in oil emulsion.

Lipase—The term "lipase" means enzymes, esterases, lipases, and phospholipases, which can cause breakdown of an emulsifier in an emulsion vaccine.

Normal Emulsion—The term "normal emulsion" means an oil in water emulsion.

Oil in Water Emulsion—The term "oil in water emulsion" means an emulsion in which small droplets of oil are suspended in a continuous water phase.

Room Temperature—The term "room temperature" means a temperature to from 18 to 25° C.

Water in Oil Emulsion—The term "water in oil emulsion" means an emulsion in which droplets of water are suspended in a continuous oil phase.

DESCRIPTION

This invention relates to bacterins with reduced lipase activity, vaccines prepared from such bacterins, and a method of reducing the lipase activity of bacterins. In addition to antigenic components, some bacterins have lipase activity. When bacterins with lipase activity are incorporated into an emulsion, the lipase may break down the emulsifiers used to create the emulsion. Emulsion vaccines that contain bacterins having high lipase activity tend to be unstable emulsions, and those that contain bacterins having low levels of lipase tend to be stable. Examples of bacteria which may, when killed, produce bacterins having lipase activity include *Aceinetobacter calcoaceticus, Acetobacter paseruianus, Aeromonas hydrophila, Alicyclobacillus acidocaldarius, Arhaeglobus fulgidus, Bacillus pumilus, Bacillus stearothermophillus, Bacillus subtilis, Bacillus thermocatenulatus, Burkholderia cepacia, Burkholderia glumae, Campylobacter coli, Campylobacter jejuni, Campylobacter hyointestinalis, Chlamydia trachomatis, Chromobacterium viscosum, Erysipelothrix rhusiopathieae, Listeria monocytogenes Escherichia coli, Haemophilus influenzae, Lawsonia intracellularis, Legionella pneumo philia, Moraxellsa* sp., *Mycoplasma hyopneumoniae, Mycoplasma mycoides* subsp. mycoides LC, *Clostridium perfringens, Photorhabdus luminescens, Propionibacterium acnes, Proteus vulgaris, Pseudomnas wisconsinensis, Pseudomonas aeruginosa, Pseudomonas fluorescens* C9, *Pseudomonas fluorescens SIKW*1, *Pseudomonas fragi, Pseudomonas luteola, Pseudomonas oleovorans, Pseudomonas* sp B11-1, *Alcaliges eutrophus, Psychrobacter immobilis, Rickettsia prowazekii, Salmonella typhimurium, Serratia marcescens, Spirlina platensis, Staphlyoccocus aureus, Staphyloccoccus epidermidis, Staphylococcus hyicus, Streptomyces albus, Streptomyces cinnamoneus, Streptomyces exfoliates, Streptomyces scabies, Sulfolobus acidocaldarius, Syechocystis* sp., *Vibrio cholerae,*

*Borrelia burgdorferi, Treponema denticola, Treponema minutum, Treponema phagedenis, Treponema refringens, Treponema vincentii, Treponema palladium*, and *Leptospira* species, such as the to known pathogens *Leptospira canicola, Leptospira grippotyposa, Leptospira hardjo, Leptospira icterohaemorrhagiae*, and *Leptospira pomona*.

The lipase, which can break down the emulsifiers used to create the emulsion, and thus cause emulsion instability and breakdown, may include one or more emulsion breaking enzymes such as esterases, lipases, and phospholipases. Collectively these enzymes, esterases, lipases, and phospholipases are referred to as lipase. The lipase activity of a bacterin may be measured using a synthetic substrate called O-pivaloyloxymethyl umbelliferone (C-POM). The rate of hydrolysis caused by the lipase is the measure of the lipase activity. The reaction rate of the hydrolysis caused by the lipase in this reaction is monitored by an increase in the fluorescence intensity of the product of the lipase activity. The reaction rate is dependent upon the exact hydrolysis test conditions chosen, so that comparisons of lipase activity levels, as measured by hydrolysis rates, should be made using data produced by the same test conditions. Literature methods are disclosed in several articles, including Kurioka S., and Matsuda M. (1976) *Ana. Biochem.* 75: 281-289, De Silva N S, and Quinn P A. (1987) *J. Clin. Microbiol.* 25: 729-731, and Grau, A., and Ortiz, A. (1998) *Chem. Phys. of Lipids.* 91: 109-118.

In an emulsion vaccine, the breakdown of the emulsion causes phase separation of the components. This is undesirable because when there is phase separation the individual doses removed from the container may not contain the same level of the vaccine components. In addition, the loss of emulsion can lead to a loss of the adjuvant activity of the emulsifier and lead to a reduction in the antigenic effect of the vaccine.

Attenuated live viruses are frequently included in vaccines along with bacterins. Such vaccines are useful because a single vaccine can be used to create immunity to different diseases with one vaccine. If the lipase activity is present in the bacterin, it will cause release of the emulsifier from the emulsion. This free emulsifier can disrupt and inactivate the live vaccine viruses, thereby leading to a loss of viral infectivity.

A bacterin useful in vaccines may be formed by culturing the bacterium of interest, and then killing the bacteria to produce a bacterin containing a variety of bacterial components, including cell wall components. The bacteria may be to killed by a variety of methods including exposing them to a compound such as merthiolate, formalin, formaldehyde, diethylamine, binary ethylenamine (BEI), beta propiolactone (BPL), and glutaraldehyde. Combinations of these compounds may be used. In addition, it is possible to kill the bacteria with sterilizing radiation.

It has now been found that the lipase activity of a bacterin having such lipase activity may be reduced by heat treatment. Specifically, the lipase activity of a bacterin may be reduced by heating the bacterin to a temperature of about 35 to about 80° C. to form a heat treated bacterin, which has acceptable antigenic activity. The heat treatment is conducted for a period of time sufficient so that the lipase activity of the heat treated bacterin is 50% or less than that found in the bacterin prior to the heat treatment. For good emulsion vaccine stability it is not necessary that the lipase activity be reduced to zero. We have found that vaccines having a good shelf life may be prepared from heat treated bacterins having lipase activity level that is 50% or less than of the lipase activity level before the heat treatment.

When a rate of hydrolysis of a test substrate has been used as a measure of the lipase activity of a bacterin, then the rate of hydrolysis of the test substrate before the heat treatment is compared to the rate of hydrolysis after the heat treatment. The heat treatment is conducted so as to reduce the rate of hydrolysis to 50% or less than the rate of hydrolysis that is observed for the fresh bacterin.

The exact method of measuring the lipase activity level is not critical as long as the same method is used to measure the activity before the heat treatment and the activity after the heat treatment. For example, if the rate of hydrolysis of a test substrate is measured using one substrate, a different substrate might produce a different rate. However, if the same substrate is used for the initial activity determination and the activity determination after treatment, the relative rates will still show the effect of the heat treatment.

For the bacterins comprising one or more of the following, *Leptospira canicola, Leptospira icterohaemorrhagiae, Leptospira grippotyphosa, Leptospira pomona*, there is a codified test for antigenic activity (9CFR §113.101, §113.102, §113.103, §113.104, and §113.105). For these species acceptable antigenic activity is defined as the ability to induce a protective immune response in vaccinated hamsters such that when hamsters are challenged with homologous live bacteria, at least 75% of the vaccinated hamsters survive in a model where at least 80% of the non-vaccinated hamsters do not survive. In the case of the antigen, *Leptospira hardjo*, acceptable antigenic activity is defined as the ability of a vaccine to induce a serological agglutination geometric mean titer against *Leptospira hardjo* of $\geq 40$ in calves that have been vaccinated with a vaccine comprising the bacterial antigen, *Leptospira hardjo*. For other bacterins acceptable antigenic activity is defined as the ability to induce a protective immune response in vaccinated animals after being challenged or by passing a codified potency test with homologous live organism.

The heat treatment may be conducted over a range of temperatures, and for a variable length of time. Generally, the heating may be done at a temperature of about 35 to about 80° C. for about 20 minutes to about 24 hours. When the bacterin is heated to a higher temperature, such as about 75 to about 80° C., the time of heating is at the short end of the time range. When the heating is done at a lower temperature, the heating is done for a longer period of time. Another combination of temperature and time is heating at a temperature of about 60 to about 70° C. for about 9 to about 10 hours. Another combination of temperature and time is heating at a temperature of about 65 to about 70° C. for about 5 to about 8 hours. Another combination of temperature and time is heating at a temperature of about 65 to about 70° C. for about one hour. Another combination of temperature and time is heating at a temperature of about 55 to about 65° C. for about 5 to about 8 hours.

The bacterins, after the heat treatment, have a lower lipase activity than freshly prepared bacterins but otherwise may be formulated in the same manner as freshly prepared bacterins. Accordingly, the heat treated bacterins may be incorporated into vaccines by ordinary methods of producing vaccines. These methods are well known in the art.

Emulsion vaccines may be formed by combining the desired bacterin with an oils phase and an emulsifier, or emulsifiers. The combination is then subjected to intense agitation to form an emulsion. Suitable agitation methods include homogenizing and subsequently microfluidizing. Preservatives and excipients may also be included in the combination prior to emulsification.

Vaccines may include both bacterins and viral antigens. In preparing a vaccine that includes bacterins and viral antigens, the bacterins, any viral antigens to be included, the emulsifier, or emulsifiers, and optionally preservatives and excipients are combined with an oil phase, and emulsified. Following emulsion formation, the pH of the formulations may be adjusted to an appropriate pH using either solutions of NaOH or HCl. For vaccine use, it is generally desirable that the pH be close to neutral to avoid irritation at the injection site. A pH of about 7.0 to about 7.3 is common.

Suitable oil phases for emulsion vaccine formation include non-metabolizable oils and metabolizable oils. The non-metabolizable oils include mineral oils, such as white mineral oil, and light mineral oil. The metabolizable oils include vegetable oils, fish oils and synthetic fatty acid glycerides.

Examples of emulsifiers that may be used in preparing emulsion vaccines of this invention are phospholipids, sorbitan esters, polyethoxylated sorbitan esters, and mannitol derivatives which are common vaccine emulsifiers. Phospholipid emulsifiers include lecithin, phosphatidylethanolamine, phosphatidylinisitol, phosphatidylserine, and lecithin, (e.g. such as AMPHIGEN®). Sorbitan ester emulsifiers include sorbitan monolaurate, (e.g. SPAN® 20 and ARLACEL® 20), sorbitan monooleate (e.g. SPAN® 80 and ARLACEL® 80), sorbitan monopalmitate (e.g. SPAN® 40 and ARLACEL® 40), and sorbitan monostearate (e.g. SPAN® 60 and ARLACEL® 60). Polyethoxylated sorbitan esters include polyethoxy sorbitan monolaurate (e.g. TWEEN® 20 and TWEEN® 21), polyethoxy sorbitan monooleate (e.g. TWEEN® 80), polyethoxy sorbitan monopalmitate (e.g. TWEEN® 40), and polyethoxy sorbitan monostearate (e.g. TWEEN® 60). Mannitol derivative emulsifiers include mannitol octadecanoic ethers. SPAN®, ARLACEL®, and TWEEN® are trademarks of ICI Americas. AMPHIGEN® is a trademark of Pfizer, Inc. Generally, vaccines are formulated as normal oil in water emulsions, although it is possible to prepare invert water in oil emulsions.

A variety of adjuvants, such as Quil A, cholesterol, aluminum phosphate, and aluminum hydroxide, and preservatives such as merthiolate may be used in vaccines. Quil A is purified mixture of quillaja saponins extracted from the bark of the South American tree Quillaja *Saponaria* Molina. Quil A acts directly on the immune system to activate a generalized state of sensitivity. In doing so, it induces both humoral and cell-mediated responses. The lipophilic chain allows interaction of antigen and adjuvant to be delivered into the cytosol for processing in an endogenous pathway. Quil A is often used with cholesterol because cholesterol eliminates the less desirable side effects when added in the appropriate proportions. Cholesterol forms insoluble complexes with Quil A that form helix-like structures as the cholesterol binds with Quil A, thus exposing the molecule's sugar units that help stimulate the immune response.

It is common to add viral antigens to vaccines containing bacterins. One advantage of this approach is that one vaccine may be used to create immunity to several diseases instead of requiring dosages of several different vaccines to achieve the same result. Both killed viruses and attenuated live viruses may be used in vaccines. Among the viruses that may be used are Avian herpesvirus, Bovine herpesviruses, Canine herpesviruses, Equine herpesviruses, Feline viral rhinotracheitis virus, Marek's disease virus, Ovine herpesviruses, Porcine herpesviruses, Pseudorabies virus, Avian paramyxoviruses, Bovine respiratory syncytial virus, Canine distemper virus, Canine parainfluenza virus, Bovine Parainfluenza 3, Ovine parainfluenza 3, Rinderpest virus, Border disease virus, Bovine viral diarrhea (BVD) virus, Classical swine fever virus, Avian Leukosis virus, Bovine immunodefieciency virus, Bovine leukemia virus, Equine infectious anemia virus, Feline immunodeficiency virus, Feline leukemia virus, Ovine progressive pneumonia virus, Ovine pulmonary adenocarcinoma virus, Canine coronavirus, Bovine coronavirus, Feline enteric coronavirus, Feline infectious peritonitis, virus, Porcine epidemic diarrhea virus, Porcine hemagglutinating encephalomyletitis virus, Porcine parvovirus, Transmissible gastroenteritis virus, Turkey coronavirus, Bovine ephemeral fever virus, Rabies, Vesicular stomatitis virus, Avian influenza, Equine influenza virus, Swine influenza virus, Canine influenza virus, Eastern Equine encephalitis virus (EEE), Venezuelan equine encephalitis virus, and Western equine encephalitis virus.

If lipase activity is present in the bacterin, it may cause release of the emulsifier from the emulsion. This free emulsifier may disrupt the live virus envelope, and inactivate the live vaccine viruses, thereby leading to a loss of viral infectivity. Accordingly, heat treatment of the bacterin serves to stabilize the emulsion, and preserve its adjuvant effect, as well as preserving the viral infectivity of the viruses.

The following examples are provided for the purpose of further illustration to and are not intended to limit the scope of the claimed invention.

Procedures

Procedure 1 Determination of Turbidity

Turbidity is determined in Nephelometric Units (NU) by a light scattering method. The intensity of light scattered by the sample under defined conditions is compared to the intensity of light scattered by a standard reference suspension. The higher the intensity of the scattered light, the higher the turbidity of the sample. A light source is directed into the sample and the light scatter is measured at 90° to the direction of the light source. The instrument is calibrated by measuring the light scatter from a formazin suspension.

Calibration of the Nephelometer Instrument

Ultra-filtered water is prepared by filtering distilled water through a membrane filter having a pore size of 0.2 μm. A first solution is prepared by dissolving 1.00 g hydrazine sulfate, $(NH_2)_2 H_2SO_4$, in ultra-filtered water and diluted with ultra-filtered water to 100 ml, in a volumetric flask. A second solution is prepared by dissolving 10.00 g. of hexamethylenetetramine in ultra-filtered water and diluting with ultra-filtered water to 100 ml, in a volumetric flask. A formazin suspension is prepared by mixing 5.0 ml of the first solution with 5.0 ml of the second solution. The mixture is allowed to stand for 24 hours at approximately 24° C. The mixture is diluted to 100 ml with ultra-filtered water to form a stock turbidity suspension having a turbidity of 400 NU. A 40 NU formazin turbidity suspension is prepared by diluting 10.00 ml of the stock turbidity suspension to 100 ml with ultra-filtered water. Further calibration solutions are prepared by diluting the stock solution.

Measurement of Turbidity

The sample to be measured is diluted with ultra-filtered water so that the turbidity falls within the calibrated range of the nephelometer. The turbidity is measured and the original turbidity is calculated using the following equation:

$$\text{Original Turbidity in } NU = \frac{M \times (D + O)}{O}$$

where:
M is the turbidity of the diluted sample in NU
D is the volume of dilution water, in mL
O is the original sample volume, in mL

Procedure 2 Lipase Analysis

Lipase activity was determined using O-pivaloxymethylumbelliferone as a fluorogenic substrate. Lipase catalyzed hydrolysis of this non-fluorescent substrate produces a hydroxymethylether, which is unstable under aqueous conditions. The decomposition of the unstable hydroxymethylether generates formaldehyde and the fluorescent product umbelliferone. Monitoring the fluorescence intensity of umbelliferone produced, as a function of time, provides a sensitive kinetic measurement of the lipase enzymatic activity.

O-pivaloxymethylumbelliferone (Molecular Probes product no. P35901) solutions were prepared in neat DMSO, at a stock concentration of 5 mM; unused solution was stored at −20° C., protected from light. The 5 mM O-pivaloxymethylumbelliferone solution was diluted to 750 µM using 58 mM TRIS-HCl buffer (pH 8.0), and the resulting solution prewarmed to 37° C. The Leptospira sample or the control buffer/medium was centrifuged for 10 minutes at room temperature at 6500× gravity to form a pellet and a supernatant. Reactions were performed by combining 15 µL of 100 mM TRIS-HCl buffer (pH 8.0) with 15 µL of the supernatant at room temperature from Leptospira sample or the control buffer/medium, in assay wells of low volume 96 well plates (Corning 3393, black polystyrene non-binding surface, half area); pre-incubating for 10 minutes at 37° C.; then initiating the reaction by the addition of 20 µL of 750 µM O-pivaloxymethylumbelliferone or the control buffer/medium. The resulting reaction mixtures contained 53 mM TRIS-HCl buffer (pH 8.0) and 0 or 300 µM O-pivaloxymethylumbelliferone. Fluorescence intensity was measured at 30-45 second intervals over a one-hour period (Spectramax Gemini XS, 37° C., $\lambda_{ex}$=360 nm, $\lambda_{em}$=460 nm, PMT sensitivity setting 'medium', 6 reads per well). The reaction rate was determined from the slope of the resulting progress curve.

EXAMPLES

Example 1

Reduction of Lipase Activity by Heat Treatment

A pool of merthiolate killed *leptospira* containing the following species *Leptospira canicola, Leptospira icterohaemorrhagiae, Leptospira grippotyphosa, Leptospira hardjo*, and *Leptospira pomona* was prepared to form a bacterin. Six samples of the bacterin were stored overnight (approximately 12 hours) at 4° C., 37° C., 45° C., 56° C., 65° C., and 80° C. The sample stored at 4° C. served as the non-treated control. The samples stored for 12 hours at 37° C., 45° C., 56° C., 65° C., and 80° C. were heat treated samples. After storage, the rate at which a test substrate hydrolysed in the presence of each bacterin was measured according to the method of Procedure 2. The rate of hydrolysis for a sample divided by the rate of hydrolysis of the sample stored at 4° C. multiplied by 100 is the percentage of the original lipase activity of each bacterin that remains after storage. The following chart shows the temperature of storage and the percentage of the original lipase activity that remains after storage.

| | Storage Temperature (12 hours) | | | | | |
|---|---|---|---|---|---|---|
| | 4° C. | 37° C. | 45° C. | 56° C. | 65° C. | 80° C. |
| Percent of Original Lipase Activity | 100% | 55.4% | 32.5% | 15.7% | 10.8% | 8.4% |

Example 2

Preparation of Experimental Vaccine Formulations

Cultures of *Leptospira canicola, Leptospira icterohaemorrhagiae, Leptospira grippotyphosa, Leptospira hardjo*, and *Leptospira pomona* were grown. The turbidity of each culture was measured in nephelometric units (NU). The bacteria were killed with merthiolate to form bacterins. Each bacterin was heat treated at 65° C. for 8 hours to reduce the lipase activity. The bacterins were combined and then mixed with AMPHIGEN®, adjuvants, preservatives, and diluting buffer so that each 5 ml dose of the vaccine contained the components set forth in the chart below.

| Component | Concentration of Component/Dose |
|---|---|
| L. canicola | 1200 NU/5 ml dose |
| L. icterohaemorrhagiae | 1200 NU/5 ml dose |
| L. grippotyphosa | 1200 NU/5 ml dose |
| L. hardjo | 2400 NU/5 ml dose |
| L. pomona | 1200 NU/5 ml dose |

The formulation was homogenized using a Silverson homogenizer and microfluidized using a microfluidizer from Microfluidics. Following both homogenization and microfluidization, the pH of the formulation was adjusted to a pH of 7.0 to 7.3.

Example 3

Potency Testing in Hamsters and Cows

The vaccine of Example 2 was administered to hamsters and cows to test for potency using standard lab and host animal models. The test hamsters were then challenged with a dose of a *Leptospira canicola, Leptospira icterohaemorrhagiae, Leptospira grippotyphosa*, or *Leptospira pomona* to test potency of the vaccines. The numbers of survivors were measured as a demonstration of efficacy. Bovine microscopic agglutination titers were measured against *Leptospira hardjo* to demonstrate the potency of that fraction of the vaccine in cows. The table below shows that vaccines prepared from heat treated *Leptospira* bacterins are capable of producing an antigenic response that passes efficacy criteria.

| Leptospira Thermal Conditioning | HAMSTER SURVIVORS | | | | BOVINE SEROLOGY |
|---|---|---|---|---|---|
| | Canicola | Icteero | Grippo | Pomona | Hardjo |
| 65° C. (8 hours) | 10/10 | 10/10 | 10/10 | 10/10 | Pass |
| Untreated | 10/10 | 10/10 | 10/10 | 10/10 | Pass |

Example 4

Physiochemical Testing of Vaccines

A vaccine was prepared from heat treated *Leptospira* bacterins according to the method of Example 2. A similar vaccine was prepared from and non-heat treated *Leptospira* bacterins according to the method of Example 2. Both vaccine formulations were stored 4° C. for 60 days. Particle size analysis was done for each vaccine when freshly prepared on day 0 and again at 60 days using a laser diffractometer.

FIG. 1 shows particle size distributions for each vaccine on day 0 before and after storage for 60 days. The vaccine prepared from heat treated *Leptospira* bacterins shows particle size retention indicating emulsion stability. The vaccine prepared from non-heat treated *Leptospira* bacterins shows an increase in particle size indicating emulsion breakdown.

Example 5

Viricidal Assay

Following the method of Example 2 vaccines were prepared from non-heat treated *Leptospira* bacterins and heat treated *Leptospira* bacterins. After 5 to 6 months of aging, the vaccines were tested for viricidal activity against BHV-1 virus, PI3 virus and BRSV virus. The viricidal activity test was performed by rehydrating monovalent viricidal assay controls (VAC), with the adjuvanted diluent to be tested. Two monovalent viricidal assay controls were rehydrated at each dose volume. The two rehydrated monovalent VACs were pooled and incubated at 20-25° C. for two hours prior to titration and inoculation on cells to determine by $TCID_{50}$ (50% tissue culture infective dose), live viral titer. It is unsatisfactory to have a viral titer loss of greater than 0.7 $TCID_{50}$/ml.

The results of the viricidal assays showing viral titer loss are listed in the table below:

| *Leptospira* Thermal Conditioning | Viral Titer Loss ($TCID_{50}$) | | |
|---|---|---|---|
| | BHV-1 | PI3 | BRSV |
| 8 hours at 65° C. | 0.1 | 0.0 | 0.4 |
| Untreated | 1.0 | ≧1.2 | ≧1.3 |

The vaccine made with non-heat treated *Leptospira* bacterins shows high levels of viricidal activity. The vaccine made with heat treated *Leptospira* bacterins was non-viricidal.

The invention claimed is:

1. An immunogenic composition which comprises:
   a) an emulsion comprising an oil and one or more emulsifiers; and
   b) a heat treated bacterin comprising a suspension of killed *Leptospira* bacteria, wherein the killed *Leptospira* bacteria are one to five *Leptospira* species selected from the group consisting of *Leptospira canicola, Leptospira grippotyposa, Leptospira hardjo, Leptospira icterohaemorrhagiae*, and *Leptospira Pomona*, wherein said bacterin has a lipase activity of 50% or less than the lipase activity of the bacterin before heat treatment, and further wherein said bacterin has acceptable antigenic activity; wherein said composition has increased stability when compared with a composition comprising a non-heat treated bacterin and:
   i) wherein the lipase activity of said bacterin is above zero; or
   ii) said bacterin is heated to a temperature of 55 to 65° C. for 5 to 8 hours, or
   iii) said bacterin is heated to a temperature of 65 to 70° C. for 5 to 8 hours, or
   iv) said bacterin is heated to a temperature of 65 to 70° C. for 1 hour, or
   v) said bacterin is heated to a temperature of 60 to 70° C. for 9 to 10 hours.

2. The immunogenic composition according to claim 1 wherein the bacterin is heated to a temperature of 55 to 65° C. for 5 to 8 hours.

3. The immunogenic composition according to claim 1 wherein the bacterin is heated to a temperature of 65 to 70° C. for 5 to 8 hours.

4. The immunogenic composition according to claim 1 wherein the bacterin is heated to a temperature of 65 to 70° C. for 1 hour.

5. The immunogenic composition according to claim 1 wherein the bacterin is heated to a temperature of 60 to 70° C. for 9 to 10 hours.

6. The immunogenic composition according to claim 1 wherein the killed *Leptospira* bacteria are one to five *Leptospira* species selected from the group consisting of *Leptospira canicola, Leptospira grippotyposa, Leptospira hardjo, Leptospira icterohaemorrhagiae*, and *Leptospira pomona*.

7. The immunogenic composition according to claim 1, wherein said one or more emulsifiers is selected from the group consisting of lecithin, sorbitan monooleate, and polyethoxy sorbitan monooleate.

8. The immunogenic composition of claim 1, wherein the heat treated bacterin is prepared by a method which comprises heating the bacterin to a temperature of 55 to 65° C. for 5 to 8 hours, or to a temperature of 65 to 70° C. for 5 to 8 hours, or to a temperature of 65 to 70° C. for 1 hour, or to a temperature of 60 to 70° C. for 9 to 10 hours.

9. The immunogenic composition of claim 1, wherein the heat treated bacterin is prepared by a method comprising the steps of:
   a) measuring the lipase activity of the bacterin;
   b) heating the bacterin to a temperature of 55 to 65° C. for 5 to 8 hours, or to a temperature of 65 to 70° C. for 5 to 8 hours, or to a temperature of 65 to 70° C. for 1 hour, or to a temperature of 60 to 70° C. for 9 to 10 hours;
   c) measuring the lipase activity of the bacterin after heat treatment;
   d) comparing the lipase activity of the bacterin before heating to the lipase activity of the bacterin after heating; and
   e) selecting a heat treated bacterin wherein the lipase activity after heat treatment is 50% or less of the lipase activity of the bacterin before heat treatment.

10. The immunogenic composition according to claim 1, wherein the heat treated bacterin is prepared by a method comprising:
    a) forming a *Leptospira* bacterin comprising a suspension of killed *Leptospira* bacteria having lipase activity; and
    b) heating the *Leptospira* bacterin to a temperature of about 55 to about 80° C. for 1 to 10 hours to reduce the lipase activity to a level of 50% or less than the level before the heat treatment.

11. The immunogenic composition according to claim 10, wherein the killed *Leptospira* bacteria are one to five *Leptospira* species selected from the group consisting of *Lep-* tospira canicola, Leptospira grippotyposa, Leptospira hardjo, Leptospira icterohaemorrhagiae, and Leptospira pomona.

12. The immunogenic composition according to claim 1, wherein the bacterin is heated to a temperature of 65° C. for 8 hours.

13. The immunogenic composition according to claim 1, wherein the heat treated bacterin is non-viricidal.

14. The immunogenic composition according to claim 7, further comprising Quil A and cholesterol.

15. The immunogenic composition according to claim 1, wherein the lipase activity of said bacterin is above zero.

\* \* \* \* \*